United States Patent
Sengupta et al.

(10) Patent No.: US 9,638,696 B2
(45) Date of Patent: May 2, 2017

(54) PROCESS FOR DETECTION AND OPTIONAL QUANTIFICATION OF AN ANALYTE

(71) Applicant: Biocon Limited, Bangalore (IN)

(72) Inventors: Nilanjan Sengupta, Bangalore (IN); Anita Rao Udiavar, Bangalore (IN); Senthil Thangamuthu, Tamil Nadu (IN); Vivek Gopal Nayak, Bangalore (IN); Ranjit Ravindran Pillai, Bangalore (IN); Laxmikant Vashishta, Bangalore (IN); Shilpa Govinda Ramaswamy, Krishnagiri (IN); Vishika Hegde, Bangalore (IN); Ramakrishnan Melarkode, Bangalore (IN)

(73) Assignee: Biocon Limited, Bangalore (IN)

(*) Notice: Subject to any disclaimer, the term of this patent is extended or adjusted under 35 U.S.C. 154(b) by 127 days.

(21) Appl. No.: 14/379,186

(22) PCT Filed: Feb. 14, 2013

(86) PCT No.: PCT/IB2013/051193
§ 371 (c)(1),
(2) Date: Aug. 15, 2014

(87) PCT Pub. No.: WO2013/121368
PCT Pub. Date: Aug. 22, 2013

(65) Prior Publication Data
US 2016/0003826 A1    Jan. 7, 2016

(30) Foreign Application Priority Data
Feb. 15, 2012 (IN) .............................. 566/CHE/2012

(51) Int. Cl.
G01N 33/53 (2006.01)
G01N 33/543 (2006.01)
G01N 33/574 (2006.01)

(52) U.S. Cl.
CPC ..... G01N 33/5748 (2013.01); G01N 33/5306 (2013.01); G01N 33/54393 (2013.01); G01N 2333/71 (2013.01)

(58) Field of Classification Search
None
See application file for complete search history.

(56) References Cited

U.S. PATENT DOCUMENTS

| | | | | |
|---|---|---|---|---|
| 4,604,348 A * | 8/1986 | Neurath | ........... | G01N 33/54393 422/400 |
| 4,657,851 A * | 4/1987 | Feller | ..................... | G01N 33/53 435/7.23 |
| 5,256,541 A * | 10/1993 | Pouletty | ........... | G01N 33/56977 435/7.24 |
| 6,866,846 B1 * | 3/2005 | Heinrich | ............. | A61M 1/3679 424/140.1 |
| 2003/0053984 A1 * | 3/2003 | Tschopp | ............... | C07K 14/472 424/85.1 |
| 2003/0125536 A1 * | 7/2003 | Fanger | ................. | C07K 14/005 536/23.2 |
| 2011/0177095 A1 * | 7/2011 | Harding | ................. | C07K 16/32 424/172.1 |

OTHER PUBLICATIONS

Baselga et al., Phase II Study of Weekly Intravenous Recombinant Humanized Anti-p185HER2 Monoclonal Antibody in Patients with HER2/neu-Overexpressing Metastatic Breast Cancer, Journal of Clinical Oncology, 14(3), (1996), p. 737-744.*

* cited by examiner

*Primary Examiner* — Christine Foster
*Assistant Examiner* — Ellen J Marcsisin
(74) *Attorney, Agent, or Firm* — Schwegman Lundberg & Woessner, P.A.

(57) ABSTRACT

The present disclosure relates to a process for detecting and optionally quantifying an analyte in a sample in the presence of a soluble target of the analyte. The soluble target forms a complex with the analyte and thus may interfere in determining the total analyte concentration. The process of the present invention utilizes a unique modified citrate buffer for diluting the sample containing the analyte and the soluble target which in turn helps in dissociating the analyte-soluble target complex, thereby enabling the process of the disclosure to detect and optionally quantify measure the analyte accurately.

12 Claims, 2 Drawing Sheets

(12) United States Patent
US 9,638,696 B2

PROCESS FOR DETECTION AND OPTIONAL QUANTIFICATION OF AN ANALYTE

PRIORITY APPLICATIONS

This application is a U.S. National Stage Filing under 35 U.S.C. 371 from International Application No. PCT/IB2013/051193, filed on 14 Feb. 2013, and published as WO/2013/121368 on 22 Aug. 2013, which application claims the benefit of priority under to Indian Application No. 566/CHE/2012, filed on 15 Feb. 2012; which applications and publication are incorporated herein by reference in their entirety.

TECHNICAL FIELD OF THE DISCLOSURE

The present disclosure relates to a process of utilizing a unique acidic dissociation buffer in a single step ligand binding assay to quantify total amount of an analyte present in a biological matrix containing a soluble target of the analyte. More specifically, the disclosure relates to a process for the development of immunoassays using an ELISA format to reliably quantify the total analyte using this unique buffer. The disclosure can be extended to immunogenicity assays for the detection of anti-analyte antibodies in the presence of excess free analyte.

BACKGROUND OF THE DISCLOSURE

Immunoassays are primarily used for the detection and quantitation of a wide variety of analytes such as hormones, tumor antigens, bacterial or viral antigens, protein therapeutics etc. in biological samples. Quantitative immunoassays are critical for understanding the Pharmacokinetic profile of the therapeutic proteins in support of efficacy and safety studies. In addition, immunoassays are also used to quantitate the soluble targets of the therapeutic proteins and anti-therapeutic protein antibodies. For soluble protein targets or shed receptor targets of the analyte, two different forms of the analyte exist in the biological matrix: the free analyte and the analyte complexed with the soluble target. In order to get an accurate pharmacokinetic profile of the analyte, it is ideal to develop ligand binding assay methods aimed at quantitating the total analyte concentrations instead of only the free analyte concentrations.

A frequent problem often encountered in quantitative immunoassays is accurate estimation of the total analyte concentrations in the presence of an interfering substance (soluble target) which competes with the immunoassay reagents for binding to the analyte. This leads to an underestimation of the analyte and compromises the true assessment of the pharmacokinetic profile of the analyte. The interfering substance can be removed by pre-treatment of the samples. However this step leads to loss of sample and introduces additional variability.

STATEMENT OF THE DISCLOSURE

Accordingly, the present disclosure relates to a process for detection and optional quantification of analyte in biological sample, said process comprising providing modified citrate buffer to the sample prior to carrying out assay for said detection and optional quantification of the analyte within the biological sample; a method of disassociating complex formed by interaction of analyte and at least one interfering substance as target for the analyte in a biological sample, said method comprising act of providing modified citrate buffer to the biological sample for disassociating the complex; an enzyme linked immunosorbent assay (ELISA) kit for detecting and optionally quantifying analyte in biological sample, said kit comprising components selected from group comprising modified citrate buffer, capture antibody, detection antibody, reagent for reacting with the detection antibody, microtitre plates, coating buffer, washing solution, and stopping solution or any combination thereof; and a modified citrate buffer for detecting and optionally quantifying presence of an analyte in a biological sample.

BRIEF DESCRIPTION OF THE ACCOMPANYING FIGURES

In order that the disclosure may be readily understood and put into practical effect, reference is made to exemplary embodiments as illustrated with reference to the accompanying figures. The figures together with a detailed description below, are incorporated in and form part of the specification, and serve to further illustrate the embodiments and explain various principles and advantages, in accordance with the present disclosure where:

FIG. 1 shows graphs depicting interference of recombinant HER2-ECD on a Trastuzumab calibration curve.

FIG. 2 is a graph showing that use of modified citrate buffer diluent results in a minimal locational shift induced by 1 µg/mL HER2-ECD spiking in serum.

DETAILED DESCRIPTION THE DISCLOSURE

Figure 1A:
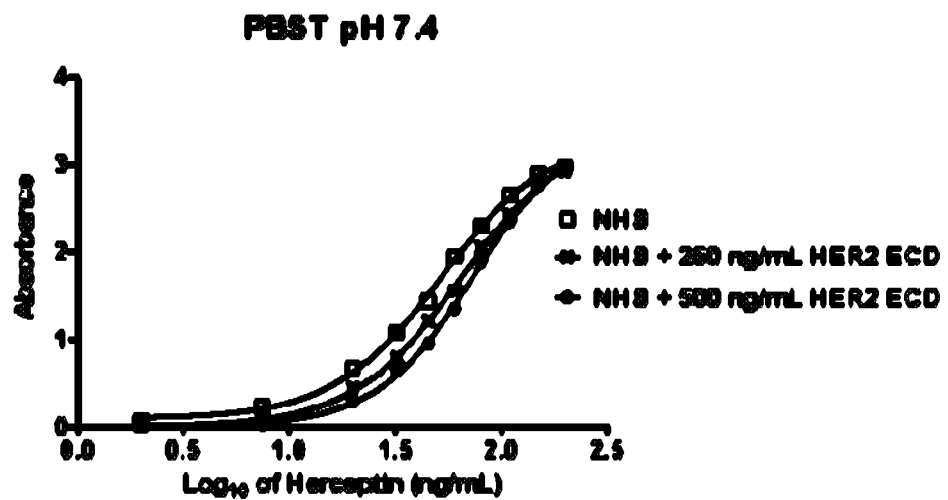
FIG. 1A shows a graph depicting that spiking of HER2-ECD results in a dose-dependent locational shift of Trastuzumab calibration curves when diluted in phosphate buffered saline Tween20 (PBST).

The present disclosure relates to a process for detection and optional quantification of an analyte in a biological sample, said process comprising providing modified citrate buffer to the sample prior to carrying out assay for said detection and optional quantification of the analyte within the biological sample.

In an embodiment of the present disclosure, the process comprises:
(a) providing modified citrate buffer to the sample for obtaining diluted biological sample; and
(b) carrying out a conventional assay for detecting and optionally quantifying the analyte in the sample.

In another embodiment of the present disclosure, the biological sample comprises at least one interfering substance as a target for the analyte, and wherein said interfering substance and said analyte combine to form a complex.

In yet another embodiment of the present disclosure, the formation of the complex reduces amount of free analyte in the biological sample, thereby hindering the accurate detection and quantification of said analyte.

In still another embodiment of the present disclosure, the modified citrate buffer dissociates the complex and restores the free analyte within the sample to enable the accurate detection and quantification of said analyte.

In still another embodiment of the present disclosure, the modified citrate buffer comprises Citrate-HCl at concentration of about 125 mM and Tween-20 at concentration of about 0.1% w/v, and wherein pH of the buffer ranges from 2.5 to 3.8, preferably 3.5.

In still another embodiment of the present disclosure, the biological sample is selected from group comprising blood, plasma, and serum or any combinations thereof.

In still another embodiment of the present disclosure, the analyte is selected from group comprising a hormone, a tumor antigen, a bacterial antigen, a viral antigen, a protein therapeutic and an antibody or any combinations thereof.

In still another embodiment of the present disclosure, the analyte is an antibody.

In still another embodiment of the present disclosure, the antibody is against human epidermal growth factor receptor 2 (HER-2).

In still another embodiment of the present disclosure, the interfering substance is an extracellular domain of HER-2 (HER-2-ECD).

In still another embodiment of the present disclosure, the assay is enzyme linked immunosorbent assay (ELISA).

In still another embodiment of the present disclosure, the enzyme linked immunosorbent assay is sandwich enzyme linked immunosorbent assay and is carried out in presence of components selected from group comprising a capture antibody, a detection antibody, a reagent for reacting with the detection antibody, a microtitre plate, a coating buffer, a washing solution and a stopping solution or any combinations thereof.

In still another embodiment of the present disclosure, the capture antibody is an antibody against the analyte within the biological sample.

In still another embodiment of the present disclosure, the detection antibody is labelled with an enzyme selected from group comprising horseradish peroxidase and alkaline phosphatase and ruthenium.

In still another embodiment of the present disclosure, the reagent for reacting with the labelled antibody is chromogenic substrate selected from ABTS (2,2'-Azinobis[3-ethylbenzothiazoline-6-sulfonic acid]-diammonium salt, TMB (3,3',5,5'-tetramethylbenzidine) and electro cheminluminscent compatible substrate.

In still another embodiment of the present disclosure, the coating buffer is phosphate buffered saline.

In still another embodiment of the present disclosure, the washing solution comprises phosphate buffered saline and Tween-20.

In still another embodiment of the present disclosure, the stopping solution is 0.1N sulphuric acid.

In still another embodiment of the present disclosure, the enzyme linked immunosorbent assay (ELISA) comprises:
  a. coating a solid surface with the capture antibody against the analyte; providing a modified citrate buffer to the biological sample for obtaining a diluted biological sample;
  b. adding the diluted sample to the antibody coated solid surface or support of step (a);
  c. incubating and washing the support to remove any unbound analyte;
  d. adding a labelled detection antibody against the analyte and washing the support to remove any unbound detection antibody; and
  e. adding a reagent for reacting with the labelled antibody for detecting and optionally quantifying the analyte in the sample.

The present disclosure further relates to a method of disassociating complex formed by interaction of analyte and at least one interfering substance as target for the analyte in a biological sample, said method comprising act of providing modified citrate buffer to the biological sample for dissociating the complex.

The present disclosure further relates to an enzyme linked immunosorbent assay (ELISA) kit for detecting and optionally quantifying an analyte in a biological sample, said kit comprising components selected from group comprising modified citrate buffer, a capture antibody, a detection antibody, reagent for reacting with the detection antibody, microtitre plates, coating buffer, washing solution, and stopping solution or any combination thereof.

The present disclosure further relates to a modified citrate buffer for detecting and optionally quantifying presence of an analyte in a biological sample.

In an embodiment of the present disclosure, the modified citrate buffer comprises citrate-HCl at concentration of about 125 mM and polysorbate-20 at concentration of about 0.1% w/v, and wherein pH of the buffer ranges from 2.5 to 3.8, preferably 3.5.

In another embodiment of the present disclosure, the biological sample comprises at least one interfering substance as a target for the analyte, and wherein said interfering substance and said analyte interact to form complex.

In yet another embodiment of the present disclosure, the analyte is a human epidermal growth factor receptor 2 (HER-2) antibody.

In still another embodiment of the present disclosure, the interfering substance is an extracellular domain of HER-2 (HER-2-ECD).

DEFINITION OF TERMS

Modified Citrate Buffer—A Modified Citrate Buffer according to the present disclosure is a citrate buffer comprising sodium citrate and citric acid also comprising polysorbate 20 and HCl. The HCl is added in order to bring down the pH of the buffer to a desired range of 2.5-3.8.

The present disclosure relates to a process of utilizing a unique acidic dissociation buffer in a single step ligand binding assay/analytical assay to accurately quantitate the total amount of an analyte present in the biological matrix containing a soluble target of the analyte (also referred to herein as interfering substance). Using this buffer resolves the problem of underestimation of the analyte due to the presence of the interfering substance, without introducing any pre-treatment of samples, thus preserving the simplicity and ease of immunoassays. The process comprises the following steps:
a) Coating a solid surface such as a microtiter plate with an antibody specific to the analyte.
b) Diluting the biological samples containing the analyte and the interfering substance in modified Citrate buffer and adding the diluted samples to the coated solid surface from the previous step.
c) Detecting the capture antibody-analyte complex by adding a labeled antibody against the analyte.
d) Adding a reagent capable of reacting with the labeled antibody and quantitating the signal.

In an embodiment of the present disclosure Modified Citrate buffer is prepared by modifying a citrate buffer by addition of a strong acid, i.e., the modified citrate buffer of the present disclosure is a combination of the salt of a weak acid (Sodium citrate) and a weak acid (citric acid) with the addition of a strong acid to obtain the required pH of between 2.5 to 3.8.

In one aspect, the modified citrate buffer contains polysorbate. In another aspect, the modified citrate buffer contains polysorbate-20.

In yet another embodiment of the present disclosure, the capture and the detection antibodies may be of monoclonal or polyclonal origin. The epitope on the analyte recognized by the detection antibody is different from the epitope recognized by the capture antibody. The label conjugated to the detection antibody may be an enzyme such as horse radish peroxidase, alkaline phosphatase or other enzymes. A substrate for the enzyme conjugated with the detection antibody is used as an indicator. Common substrates used are selected from ABTS (2,2'-Azinobis[3-ethylbenzothiazoline-6-sulfonic acid]-diammonium salt and TMB (3,3',5,5'-tetramethylbenzidine).

In still another embodiment, the present disclosure relates to a process of utilizing a unique acidic dissociation buffer in a single step ligand binding assay to quantitate total amount of analyte present in the serum matrix containing the interfering substance.

In still another embodiment, the disclosure discloses a method of accurately determining the levels of an anti-HER2 antibody in the presence of an interfering substance, an extracellular domain (ECD) of HER2 receptors. The biological sample in which the accurate determination of the level of anti-HER2 antibody is sought may be serum or plasma derived from a cancer patient undergoing anti-HER2 therapy.

In still another embodiment of the present disclosure, accuracy (analytical recovery) of trastuzumab QCs made in metastatic breast cancer sera containing endogenous HER2-ECD is maximum when modified citrate buffer is used as diluent.

The present disclosure is illustrated by its application to the accurate analytical recovery of trastuzumab in serum spiked with recombinant HER2-ECD, the soluble target of trastuzumab. Over-expression of the human epidermal growth factor receptor 2 (HER-2/neu) occurs in 25% of human breast cancers and is associated with poor prognosis. Trastuzumab is a humanized monoclonal antibody against the extracellular domain (ECD) of HER-2/neu receptor and binding results in inhibition of cancer cell proliferation. Trastuzumab is approved for the treatment of HER-2/neu over-expressing Metastatic Breast Cancer. The concentration of serum trastuzumab should be maintained above 10 µg/mL during therapy, in order to effectively inhibit the growth of HER-2/neu over-expressing breast cancer cells. Accurate quantitation of serum trastuzumab concentrations is hence critical during therapy.

In an embodiment of the present disclosure, the full length HER-2/neu protein is composed of a cytoplasmic domain, a transmembrane domain and an extracellular domain (ECD) that is shed from the surface of cells. ECD is shed into the blood of normal individuals and is often elevated in metastatic breast cancer patients. Trastuzumab administered for treatment of these patients exists in two different forms in the matrix, the free drug and the drug complexed with the ECD. Elevated levels of circulating endogenous ECD result in increased levels of complexed trastuzumab. Standard immunoassays for quantitating trastuzumab measure only free trastuzumab leading to the underestimation of the circulating total trastuzumab levels. The assay disclosed herein eliminates the problem of ECD interference and thus underestimation by utilizing a unique acid-dissociation buffer which dissociates the trastuzumab-ECD complex in a single step.

The present disclosure is further elaborated with the help of following examples and associated figures. However, these examples should not be construed to limit the scope of the present disclosure.

EXAMPLES

Example 1

Preparation of Modified Citrate Buffer

In the present disclosure, 13.04 g of Citric Acid Monohydrate and 18.48 g of Sodium Citrate Dihydrate are added to 950 mL of Milli Q water and dissolved. The pH of the solution is adjusted to 3.5 by adding Concentrated HCl (~4 mL). The volume of the solution is made up to 1000 ml and the solution is filtered using 0.22 Micron filter unit to obtain the modified citrate buffer.

Example 2

Single Step ELISA for Accurate Quantitation of Trastuzumab in the Presence of Interfering HER2-ECD In the present disclosure, 100 µL of a monoclonal antibody against trastuzumab Complementary Determining region (CDR) is coated on 96 well microtiter plates in PBS buffer at a final concentration of about 1 µg/mL and incubated overnight at about 4° C. Calibrators and Quality Controls (QC) are prepared using trastuzumab in serum samples spiked with or without recombinant HER2-ECD. Samples are diluted about 50 fold (minimum required dilution, MRD) in modified citrate buffer containing 125 mM citrate-HCl and 0.1% Tween-20 (polysorbate 20) at pH between 2.8 to 3.5, and added to the blocked antibody coated microtiter plates. The plates are incubated at 22° C. for one hour and washed five times with PBST. After washing, about 100 µL of Peroxidase conjugated polyclonal detection antibody against trastuzumab CDR (1:2500 in PBST) is added to each well and incubated at 22° C. for one hour. The plates are washed seven times with PBST and about 100 µL of chromogenic substrate TMB is added to each well. After an incubation of 15 minutes, the reaction is stopped by the addition of 0.1N Sulphuric Acid and the plate is read at 450 nm with a background subtraction at 630 nm.

Example 3

Investigation of Interference of HER2-ECD on Serum Calibration Curve of Trastuzumab and Studying the Effect of Modified Citrate Buffer on the Same In the present disclosure, in order to investigate the interference of HER2-ECD on the serum calibration curve of trastuzumab, trastuzumab calibration curves are made in pooled healthy female serum containing either 0 ng/mL, 250 ng/mL and 500 ng/mL of spiked recombinant HER2-ECD. Samples are made to undergo 50 fold MRD in appropriate diluents—FIG. 1. The Trastuzumab calibration curve was done using the ELISA assay as described above.

Figure 1B:
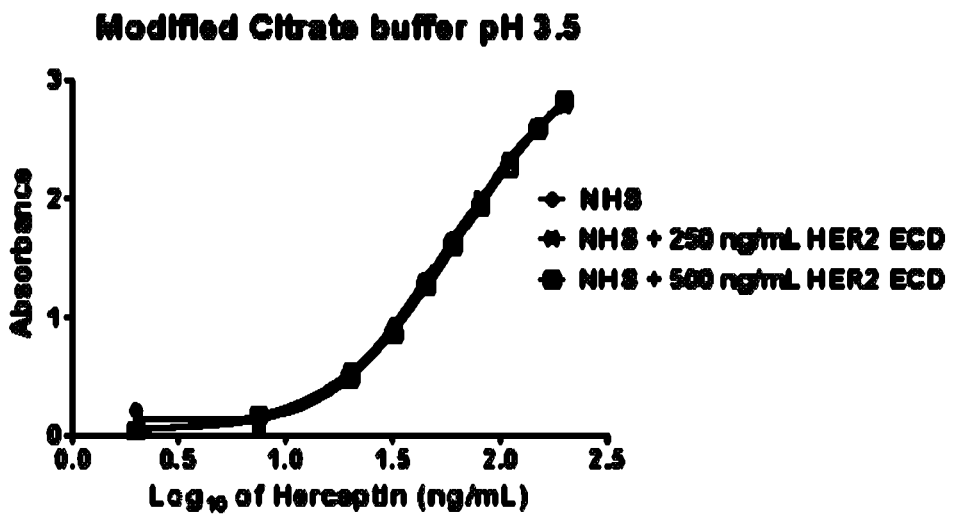
FIG. 1B shows a graph depicting that modified citrate buffer diluent nullifies the dose-dependent interference of HER2-ECD on a Trastuzumab calibration curve.

FIG. 1A) shows that increasing the amount of spiked recombinant HER2-ECD resulted in a locational shift of the Trastuzumab Calibration curves in PBST diluent. FIG. 1B) shows that the interference of spiked HER2-ECD is overcome when the serum samples underwent the MRD in modified citrate buffer (pH 3.5) diluent containing polysorbate 20. Dilution of samples containing spiked HER2-ECD and trastuzumab in modified citrate buffer containing polysorbate 20 resulted in the dissociation of immune complex formed between the analyte (trastuzumab) and target (HER2-ECD).

Example 4

Determining the Optimal Acidic pH of Buffer for Disassociating Trastuzumab—HER2-ECD Complex In the present disclosure, to determine the optimal acidic pH required to dissociate the trastuzumab—HER2-ECD complex, an acidic buffer, Citrate is tested at three different pH values as assay diluents for MRD. PBST diluent is also used as a control. Trastuzumab calibration curves are made in serum without spiked HER2-ECD and trastuzumab QC samples (500 ng/mL in neat serum) are prepared in 500 ng/mL recombinant HER2-ECD spiked serum. Calibration standards and QCs are made to undergo MRD in each of the four diluents. Analytical recovery of QC samples in each diluent is back calculated from the calibration curve prepared in the corresponding diluent. The lower the percentage relative error of recovery of trastuzumab QC, the better the buffer. As shown in table 1 above, a pH of 2.5 to 3.8 is required to obtain maximum recovery of the trastuzumab QC samples made in HER2-ECD spiked serum, with a pH of 3.5 showing the best result. The Trastuzumab calibration curve was done using the ELISA assay as described above.

TABLE 1

Optimum pH of Assay Diluent for Maximum Analytical Recovery of Trastuzumab LLOQ-QC (Lower Limit of Quantitation Quality Control)

| S. No | Buffer | pH | % Analytical Recovery of trastuzumab QC (500 ng/ml) in 500 ng/ml HER2 ECD spiked serum | % Relative error of recovery of trastuzumab QC (500 ng/mL) in 500 ng/mL HER2 ECD spiked serum |
|---|---|---|---|---|
| 1 | PBST | 7.4 | 32.4 | 67.6 |
| 2 | Citrate buffer + 0.1% polysorbate-20 | 4.5 | 46.5 | 53.5 |
| 3 | Modified Citrate + 0.1% polysorbate-20 | 4.0 | 74.78 | 25.22 |
| 4 | Modified Citrate + 0.1% polysorbate-20 | 3.8 | 90.29 | 9.71 |
| 5 | Modified Citrate + 0.1% polysorbate-20 | 3.5 | 104.67 | 4.67 |
| 6 | Modified Citrate + 0.1% polysorbate-20 | 3.0 | 108.41 | 8.41 |
| 7 | Modified Citrate + 0.1% polysorbate-20 | 2.5 | 88.77 | 11.23 |
| 8 | Modified Citrate + 0.1% polysorbate-20 | 2.0 | ND | ND |

Example 5

Comparison of Buffers for Obtaining Maximum Analytical Recovery of Trastuzumab QC In the present disclosure, various acidic buffers at pH 3.5 are compared for MRD of samples to assess the most suitable combination of salt and weak acid in order to nullify the interference by HER2-ECD and maximize the analytical recovery of QC samples. Trastuzumab calibration curve, trastuzumab QCs (500 ng/mL and 1500 ng/mL in neat serum) are made in 1 µg/mL HER2-ECD spiked serum and made to undergo 50 fold MRD in four different diluents. The ELISA assay also includes a control trastuzumab calibration curve made in serum without spiked HER2-ECD and diluted 50 fold in PBST. Analytical recovery of QC samples in each diluent is back calculated from the control trastuzumab calibration curve made in serum without spiked HER2-ECD and diluted 50 fold in PBST.

Figure 2:
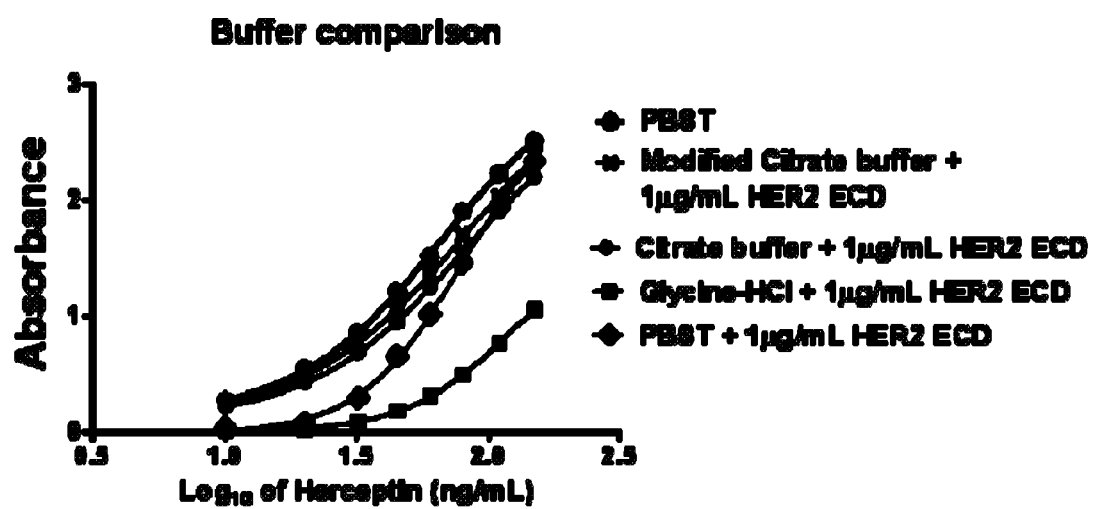
FIG. 2 shows the comparison of different acidic buffers at pH 3.5, to nullify the interference of recombinant HER2-ECD on a Trastuzumab calibration curve. Particularly.

FIG. 2 shows that usage of Modified citrate buffer diluent results in minimal calibration curve shift induced by 1 µg/mL HER2-ECD spike, as compared to the control un-spiked serum calibration curve diluted in PBST.

In the present disclosure, dilution of samples in other acidic buffers of same pH (conventional citrate buffer without the addition of HCl and glycine-HCl) failed to nullify the HER2-ECD induced calibration curve shift as shown in Table 2 below. Maximum recovery of the Trastuzumab QC samples (500 ng/mL and 1500 ng/mL in neat serum) is observed when modified citrate buffer diluent is used.

TABLE 2

Comparison of Various Buffers for Obtaining Maximum Analytical Recovery of Trastuzumab QC

| | | % Analytical Recovery of Trastuzumab QCs in 1 µg/ml HER2-ECD spiked serum | |
|---|---|---|---|
| S. No. | Buffer | LLOQ QC (500 ng/ml) | LOW QC (1500 ng/ml) |
| 1 | PBST | 10.28 | 40.97 |
| 2 | Glycine HCl, pH 3.5 | Out of Range | 9.82 |
| 3 | Citrate buffer + 0.1% polysorbate 20 pH 3.5 | 72.56 | 75.16 |
| 4 | Modified Citrate buffer + 0.1% polysorbate 20 pH 3.5 | 86.06 | 86.82 |

This emphasizes the criticality of the modified citrate buffer composition on trastuzumab QC recovery in the presence of HER2-ECD.

Example 6

HER2-ECD Tolerance Determination of the Modified Immunoassay Using Modified Citrate Buffer Diluent In the present disclosure, to determine the maximum concentration of shed HER2-ECD that can be tolerated by the improved immunoassay using modified citrate buffer diluent containing polysorbate 20, trastuzumab QCs (375 ng/mL, 1125 ng/mL and 7500 ng/mL) are made in serum samples containing increasing amounts of recombinant HER2-ECD. The calibration standards and QC samples are made to undergo a 50 fold MRD in modified citrate buffer containing polysorbate 20. The analytical recoveries of QCs are back-calculated from a trastuzumab calibration curve made in un-spiked serum. It is observed that trastuzumab QCs can be reliably recovered from samples containing up to 2 µg/mL of HER2-ECD as shown in Table 3 below. The assay used in this experiment is ELISA.

TABLE 3

HER2-ECD Tolerance Determination of the Modified
Immunoassay using Modified Citrate Buffer Diluent

| | Spiked HER2-ECD level | % Analytical Recovery of Trastuzumab QCs in recombinant HER2-ECD spiked samples | | |
|---|---|---|---|---|
| S. No. | (ng/ml) | 375 ng/ml | 1125 ng/ml | 7500 ng/ml |
| 1 | 50 | 106.11 | 100.37 | 93.11 |
| 2 | 500 | 97.11 | 98.27 | 95.04 |
| 3 | 1000 | 96.45 | 94.49 | 94.64 |
| 4 | 2000 | 98.01 | 92.09 | 95.30 |

Example 7

Analytical Recovery of Trastuzumab QC in Metastatic Breast Cancer Patient Samples with Varying Levels of Shed HER2-ECD In the present disclosure, analytical Recovery of trastuzumab QCs made in Metastatic Breast Cancer (MBC) serum samples containing varying levels of endogenous shed HER2-ECD is shown in Table 4 below. A trastuzumab calibration curve made in un-spiked pooled healthy female sera and trastuzumab QCs made in MBC serum samples are diluted 50 fold using either PBST or modified citrate buffer containing polysorbate 20. The analytical recoveries of QCs are back-calculated from the corresponding diluent calibration curve. As seen in table 4 below, usage of modified Citrate buffer diluent results in optimal Trastuzumab QC recoveries compared to PBST diluent. The assay performed is ELISA. The concentrations of endogenous shed HER2-ECD are evaluated in MBC patient samples by a commercially available ELISA kit.

TABLE 4

Analytical recovery of Trastuzumab QC in metastatic breast cancer patient samples with varying levels of shed HER2-ECD. Usage of modified Citrate buffer diluent resulted in optimal Trastuzumab QC recoveries compared to PBST diluent.

| | Shed HER2- | % Analytical Recovery of Trastuzumab QCs in metastatic breast cancer patients at LLOQ QC (500 ng/mL) | |
|---|---|---|---|
| Patient No | ECD level (ng/mL) | PBST diluent | Modified Citrate buffer diluent containing polysorbate 20 |
| 1 | 33.7 | 95.02 | 99.93 |
| 2 | 56.8 | 87.37 | 97.02 |
| 3 | 77.5 | 86.23 | 100 |
| 4 | 170 | 83.02 | 103.32 |
| 5 | 211.6 | 74.22 | 95.3 |
| 6 | 580 | 67.06 | 106.17 |
| 7 | 716.9 | ND | 104.48 |
| 8 | 833.6 | ND | 95.09 |
| 9 | 4761.8 | BQL | 87.29 |

*ND: Not done;
BQL: Below Quantitation Limit.

Therefore, from the above examples, it is clear that the process of the present disclosure utilizing the modified citrate buffer is capable of accurately determining and quantifying analytes, such as HER-2 antibody in a biological sample which contains a soluble target for the analyte such as HER-2 ECD. It is observed that Trastuzumab QCs can be reliably recovered from samples containing up to 4.7 µg/mL of HER2-ECD as shown in Table 4 above.

OTHER EMBODIMENTS

While a number of embodiments and examples of this invention are described herein, it is apparent that these embodiments and examples may be altered to provide additional embodiments and examples which use the processes of this invention. Therefore it will be appreciated that the scope of this invention is to be defined by the appended claims, rather than by the specific embodiments that have been represented by way of example above.

We claim:

1. A process for detection and quantification of trastuzumab in a biological sample, said process comprising:
    (a) diluting the biological sample with a modified citrate buffer comprising citrate-HCl at a concentration of about 125 mM and polysorbate-20 at a concentration of about 0.1% w/v, the modified citrate buffer having a pH of 3.5, and
    (b) performing an assay to detect and quantify trastuzumab in the biological sample,
    wherein the biological sample comprises at least one interfering substance that binds trastuzumab, wherein the at least one interfering substance is an extracellular domain of HER-2 (HER-2-ECD) and wherein said interfering substance and trastuzumab combine to form a complex in the biological sample.

2. The process of claim 1, wherein the modified citrate buffer dissociates the complex to enable accurate detection and quantification of trastuzumab.

3. The process of claim 1, wherein the biological sample is selected from the group consisting of blood, plasma, serum or a combination thereof.

4. The process of claim 1, wherein the assay is an enzyme linked immunosorbent assay (ELISA).

5. The process of claim 4, wherein the ELISA is a sandwich ELISA and is carried out in presence of components selected from the group consisting of capture antibody, detection antibody, reagent for reacting with the detection antibody, microtitre plate, coating buffer, washing solution and stopping solution.

6. The process of claim 5, wherein the capture antibody is an antibody that binds to trastuzumab.

7. The process of claim 5, wherein the detection antibody is labelled with a label selected from the group consisting of horseradish peroxidase, alkaline phosphatase, or ruthenium.

8. The process of claim 5, wherein the reagent for reacting with the detection antibody is a chromogenic substrate selected from the group consisting of ABTS (2,2'-Azinobis [3-ethylbenzothiazoline-6-sulfonic acid]-diammonium salt) and TMB (3,3',5,5'-tetramethylbenzidine).

9. The process of claim 5, wherein the reagent for reacting with the detection antibody is an electrochemiluminescent substrate.

10. The process of claim 5, wherein the coating buffer is phosphate buffered saline.

11. The process of claim 5, wherein the washing solution comprises phosphate buffered saline and polysorbate-20.

12. The process of claim 5, wherein the stopping solution is 0.1 N sulphuric acid.

* * * * *